United States Patent
Inoue et al.

(10) Patent No.: US 12,303,336 B2
(45) Date of Patent: May 20, 2025

(54) ULTRASOUND DIAGNOSTIC APPARATUS AND CONTROL METHOD OF ULTRASOUND DIAGNOSTIC APPARATUS

(71) Applicant: FUJIFILM Corporation, Tokyo (JP)

(72) Inventors: Tomoki Inoue, Kanagawa (JP); Katsuya Yamamoto, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 187 days.

(21) Appl. No.: 18/358,318

(22) Filed: Jul. 25, 2023

(65) Prior Publication Data

US 2023/0363740 A1 Nov. 16, 2023

Related U.S. Application Data

(63) Continuation of application No. PCT/JP2022/000200, filed on Jan. 6, 2022.

(30) Foreign Application Priority Data

Feb. 2, 2021 (JP) ................................ 2021-014723

(51) Int. Cl.
*A61B 8/00* (2006.01)
*A61B 8/08* (2006.01)

(52) U.S. Cl.
CPC ............ *A61B 8/5207* (2013.01); *A61B 8/085* (2013.01); *A61B 8/461* (2013.01)

(58) Field of Classification Search
CPC ....... A61B 8/5207; A61B 8/085; A61B 8/461; A61B 8/06; A61B 8/0841; A61B 8/14;
(Continued)

(56) References Cited

U.S. PATENT DOCUMENTS

2010/0063355 A1* 3/2010 Matsuura ............. A61B 1/0638
  600/109
2011/0150274 A1* 6/2011 Patwardhan ............ G06T 7/149
  382/209
(Continued)

FOREIGN PATENT DOCUMENTS

JP 2012-090821 A 5/2012
JP 2015-154883 A 8/2015
(Continued)

OTHER PUBLICATIONS

International Search Report issued in PCT/JP2022/000200; mailed Mar. 29, 2022.
(Continued)

*Primary Examiner* — Joseph M Santos Rodriguez
*Assistant Examiner* — Zainab Mohammed Aldarraji
(74) *Attorney, Agent, or Firm* — Studebaker Brackett PLLC

(57) ABSTRACT

In an ultrasound diagnostic apparatus and a control method of the ultrasound diagnostic apparatus of the present invention, a blood vessel extraction unit extracts a short-axis image of a blood vessel from an ultrasound image, an emphasis display unit displays in an emphasized manner the short-axis image of the blood vessel in the ultrasound image displayed on a monitor, and a movement amount detection unit detects a movement amount of the ultrasound image between adjacent frames on the basis of the ultrasound image. In a case where the movement amount is equal to or greater than a first threshold value after the emphasis display of the short-axis image of the blood vessel by the emphasis display unit is started, the apparatus control unit stops the emphasis display of the short-axis image of the blood vessel by the emphasis display unit. As a result, the short-axis image of the blood vessel included in the ultrasound image can be displayed in an emphasized manner without causing
(Continued)

a user to feel discomfort even in a case where the entire ultrasound image is moved.

20 Claims, 4 Drawing Sheets

(58) Field of Classification Search
CPC ....... A61B 8/4483; A61B 8/463; A61B 8/467; A61B 8/469; A61B 8/5223; A61B 8/0891
See application file for complete search history.

(56) References Cited

U.S. PATENT DOCUMENTS

| | | | |
|---|---|---|---|
| 2011/0245673 A1* | 10/2011 | Kamiyama | G01S 7/52071 600/443 |
| 2012/0108970 A1 | 5/2012 | Miyama et al. | |
| 2015/0238165 A1* | 8/2015 | Hyuga | A61B 8/4245 600/449 |
| 2016/0015337 A1 | 1/2016 | Inoue et al. | |
| 2017/0091914 A1 | 3/2017 | Halmann et al. | |
| 2021/0137492 A1 | 5/2021 | Imai | |
| 2021/0196228 A1* | 7/2021 | Raju | A61B 5/33 |
| 2022/0104789 A1* | 4/2022 | Matsumoto | A61B 8/0891 |
| 2024/0065671 A1* | 2/2024 | Matsumoto | A61B 8/0891 |

FOREIGN PATENT DOCUMENTS

| | | |
|---|---|---|
| JP | 2018-023610 A | 2/2018 |
| WO | 2014/162365 A1 | 10/2014 |
| WO | 2016/013055 A1 | 1/2016 |
| WO | 2017/138086 A1 | 8/2017 |
| WO | 2020/044769 A1 | 3/2020 |
| WO | 2021/014767 A1 | 1/2021 |

OTHER PUBLICATIONS

International Preliminary Report on Patentability (Chapter I) and Written Opinion of the International Searching Authority issued in PCT/JP2022/000200; issued Aug. 3, 2023.

The extended European search report issued by the European Patent Office on May 24, 2024, which corresponds to European Patent Application No. 22749400.2-1122 and is related to U.S. Appl. No. 18/358,318.

* cited by examiner

ULTRASOUND DIAGNOSTIC APPARATUS AND CONTROL METHOD OF ULTRASOUND DIAGNOSTIC APPARATUS

CROSS-REFERENCE TO RELATED APPLICATIONS

This application is a Continuation of PCT International Application No. PCT/JP2022/000200 filed on Jan. 6, 2022, which claims priority under 35 U.S.C. § 119(a) to Japanese Patent Application No. 2021-014723 filed on Feb. 2, 2021. The above applications are hereby expressly incorporated by reference, in their entirety, into the present application.

BACKGROUND OF THE INVENTION

1. Field of the Invention

The present invention relates to an ultrasound diagnostic apparatus and a control method of the ultrasound diagnostic apparatus which have a function of extracting a short-axis image of a blood vessel included in an ultrasound image and displaying in an emphasized manner the short-axis image.

2. Description of the Related Art

For example, in a case where a puncture needle or the like is inserted into a blood vessel of a subject, in order to determine a puncture position and the thickness of the puncture needle, the diameter, depth, type (artery or vein), and the like of the blood vessel are checked while observing the ultrasound image using the ultrasound diagnostic apparatus. However, interpretation of ultrasound images requires skill, and interpretation of ultrasound images is not easy for an unskilled person. Therefore, as disclosed in JP2012-090821A, JP2018-023610A, JP2015-154883A, and WO2014/162365A, an ultrasound diagnostic apparatus has been proposed that extracts a short-axis image of a blood vessel from an ultrasound image and detects the movement of the blood vessel or the like. There is also a technique of providing a position sensor in an ultrasound probe and detecting the movement of the ultrasound probe.

SUMMARY OF THE INVENTION

Here, a case is considered in which a short-axis image of a blood vessel is extracted from an ultrasound image including the short-axis image of the blood vessel, and the short-axis image of the blood vessel is displayed in an emphasized manner.

Ultrasound images are generated at a constant speed (frame rate) of, for example, 30 frames/second. On the other hand, processing of extracting short-axis images of blood vessels from the ultrasound images requires some time. Therefore, in a case where a short-axis image of a blood vessel is extracted from an ultrasound image and the short-axis image of the blood vessel is displayed in an emphasized manner, the short-axis image of the blood vessel is displayed in an emphasized manner with a slight time delay with respect to the ultrasound image in the real frame time that is generated at a constant speed.

However, in a case where the entire ultrasound image is moved, such as by moving the ultrasound probe by a user, in a case where the extraction and the emphasis display of the short-axis image of the blood vessel are performed with a delay with respect to the display of the ultrasound image, the position where the emphasis display is performed greatly deviates from the position of the short-axis image of the blood vessel included in the ultrasound image in the real frame time that is currently displayed on a monitor, and thus there is a problem that the user who is looking at the ultrasound image displayed on the monitor feels discomfort.

An object of the present invention is to provide an ultrasound diagnostic apparatus and a control method of the ultrasound diagnostic apparatus which can display in an emphasized manner a short-axis image of a blood vessel included in an ultrasound image without causing a user to feel discomfort even in a case where the entire ultrasound image is moved.

In order to achieve the object, an aspect of the present invention provides an ultrasound diagnostic apparatus comprising an ultrasound probe; a monitor; an image generation unit that generates an ultrasound image including a short-axis image of a blood vessel on the basis of a reception signal obtained by performing transmission and reception of ultrasound beams with respect to a subject using the ultrasound probe; a display control unit that displays the ultrasound image on the monitor; a blood vessel extraction unit that extracts the short-axis image of the blood vessel from the ultrasound image; an emphasis display unit that displays in an emphasis manner the short-axis image of the blood vessel in the ultrasound image displayed on the monitor; a movement amount detection unit that detects a movement amount of the ultrasound image between adjacent frames on the basis of the ultrasound image; and an apparatus control unit that, in a case where the movement amount is equal to or greater than a first threshold value after the emphasis display of the short-axis image of the blood vessel by the emphasis display unit is started, stops the emphasis display of the short-axis image of the blood vessel by the emphasis display unit.

It is preferable that, in a case where the movement amount is less than the first threshold value, the blood vessel extraction unit detects the short-axis image of the blood vessel as an observation target from the short-axis images of the blood vessels extracted from the ultrasound image, and the movement amount detection unit detects the movement amount by tracking the short-axis image of the blood vessel as the observation target over ultrasound images of a plurality of frames.

It is preferable that, in a case where short-axis images of a plurality of blood vessels are extracted from the ultrasound image, the movement amount detection unit detects an average value of movement amounts of the short-axis images of the plurality of blood vessels as the movement amount of the ultrasound image.

It is preferable that, after the emphasis display of the short-axis image of the blood vessel by the emphasis display unit is stopped, in a case where the movement amount is equal to or less than a second threshold value lower than the first threshold value, the apparatus control unit restarts the emphasis display of the short-axis image of the blood vessel by the emphasis display unit.

It is preferable that, after the emphasis display of the short-axis image of the blood vessel by the emphasis display unit is stopped, in a case where the movement amount is equal to or greater than a third threshold value greater than the first threshold value, the apparatus control unit stops the extraction of the short-axis image of the blood vessel by the blood vessel extraction unit.

It is preferable that, after the emphasis display of the short-axis image of the blood vessel by the emphasis display unit is started, in a case where the movement amount is equal to or less than a fourth threshold value lower than the first threshold value, the apparatus control unit executes the extraction of the short-axis image of the blood vessel by the blood vessel extraction unit and the emphasis display of the short-axis image of the blood vessel by the emphasis display unit for each ultrasound image of a predetermined plurality of frames.

It is preferable that the blood vessel extraction unit includes a blood vessel identification unit that determines whether or not the blood vessel included in each ultrasound image of adjacent frames is the same blood vessel on the basis of the short-axis image of the blood vessel extracted from each ultrasound image of the adjacent frames, and displays in an emphasized manner the short-axis image of the blood vessel determined to be the same.

It is preferable that the movement amount detection unit detects a difference between central coordinates or barycentric coordinates of the short-axis image of the blood vessel extracted from each ultrasound image of adjacent frames, a difference between coordinates of a feature point included in each ultrasound image of the adjacent frames, or an optical flow of the ultrasound image between the adjacent frames, as the movement amount of the ultrasound image.

It is preferable that the ultrasound diagnostic apparatus further includes a blood vessel information acquisition unit that acquires blood vessel information regarding the blood vessel included in the ultrasound image, and the emphasis display unit displays the blood vessel information on the monitor in addition to the emphasis display of the short-axis image of the blood vessel.

It is preferable that the ultrasound diagnostic apparatus further includes a notification unit that notifies a user of notification information regarding a movement speed of the ultrasound probe on the basis of the movement amount.

Another aspect of the present invention provides a control method of an ultrasound diagnostic apparatus, the control method comprising: generating an ultrasound image including a short-axis image of a blood vessel on the basis of a reception signal obtained by performing transmission and reception of ultrasound beams with respect to a subject using an ultrasound probe; displaying the ultrasound image on a monitor; extracting the short-axis image of the blood vessel from the ultrasound image; displaying in an emphasis manner the short-axis image of the blood vessel in the ultrasound image displayed on the monitor; detecting a movement amount of the ultrasound image between adjacent frames on the basis of the ultrasound image; and stopping, in a case where the movement amount is equal to or greater than a first threshold value after the emphasis display of the short-axis image of the blood vessel is started, the emphasis display of the short-axis image of the blood vessel.

It is preferable that in a case where the movement amount is less than the first threshold value, the short-axis image of the blood vessel as an observation target is detected from the short-axis images of the blood vessels extracted from the ultrasound image, and the movement amount is detected by tracking the short-axis image of the blood vessel as the observation target over ultrasound images of a plurality of frames.

It is preferable that, in a case where short-axis images of a plurality of blood vessels are extracted from the ultrasound image, an average value of the movement amounts of the short-axis images of the plurality of blood vessels is detected as the movement amount of the ultrasound image.

It is preferable that, after the emphasis display of the short-axis image of the blood vessel is stopped, in a case where the movement amount is equal to or less than a second threshold value lower than the first threshold value, the emphasis display of the short-axis image of the blood vessel is restarted.

It is preferable that, after the emphasis display of the short-axis image of the blood vessel is stopped, in a case where the movement amount is equal to or greater than a third threshold value greater than the first threshold value, the extraction of the short-axis image of the blood vessel is stopped.

It is preferable that, after the emphasis display of the short-axis image of the blood vessel is started, in a case where the movement amount is equal to or less than a fourth threshold value lower than the first threshold value, the extraction of the short-axis image of the blood vessel and the emphasis display of the short-axis image of the blood vessel are executed for each ultrasound image of a predetermined plurality of frames.

It is preferable that, whether or not the blood vessel included in each ultrasound image of adjacent frames is the same blood vessel is determined on the basis of the short-axis image of the blood vessel extracted from each ultrasound image of the adjacent frames, and the short-axis image of the blood vessel determined to be the same is displayed in an emphasized manner.

It is preferable that a difference between central coordinates or barycentric coordinates of the short-axis image of the blood vessel extracted from each ultrasound image of adjacent frames, a difference between coordinates of a feature point included in each ultrasound image of the adjacent frames, or an optical flow of the ultrasound image between the adjacent frames is detected as the movement amount of the ultrasound image.

It is preferable that the control method further includes acquiring blood vessel information regarding the blood vessel included in the ultrasound image, and the blood vessel information is displayed on the monitor in addition to the emphasis display of the short-axis image of the blood vessel.

It is preferable that a user is notified of notification information regarding a movement speed of the ultrasound probe on the basis of the movement amount.

In the present invention, in a case where the movement amount is equal to or greater than a first threshold value after the emphasis display of the short-axis image of the blood vessel by the emphasis display unit is started, the emphasis display of the short-axis image of the blood vessel by the emphasis display unit is stopped. As a result, according to the present invention, even in a case where the movement amount of the ultrasound image is increased, the emphasis display will not be displayed with a large deviation from the position of the short-axis image of the blood vessel included in the ultrasound image in the real frame time, the user will not feel discomfort.

DESCRIPTION OF THE PREFERRED EMBODIMENTS

Hereinafter, an ultrasound diagnostic apparatus and a control method of the ultrasound diagnostic apparatus according to the present invention will be described in detail on the basis of preferred embodiments illustrated in the accompanying drawings.

Figure 1:
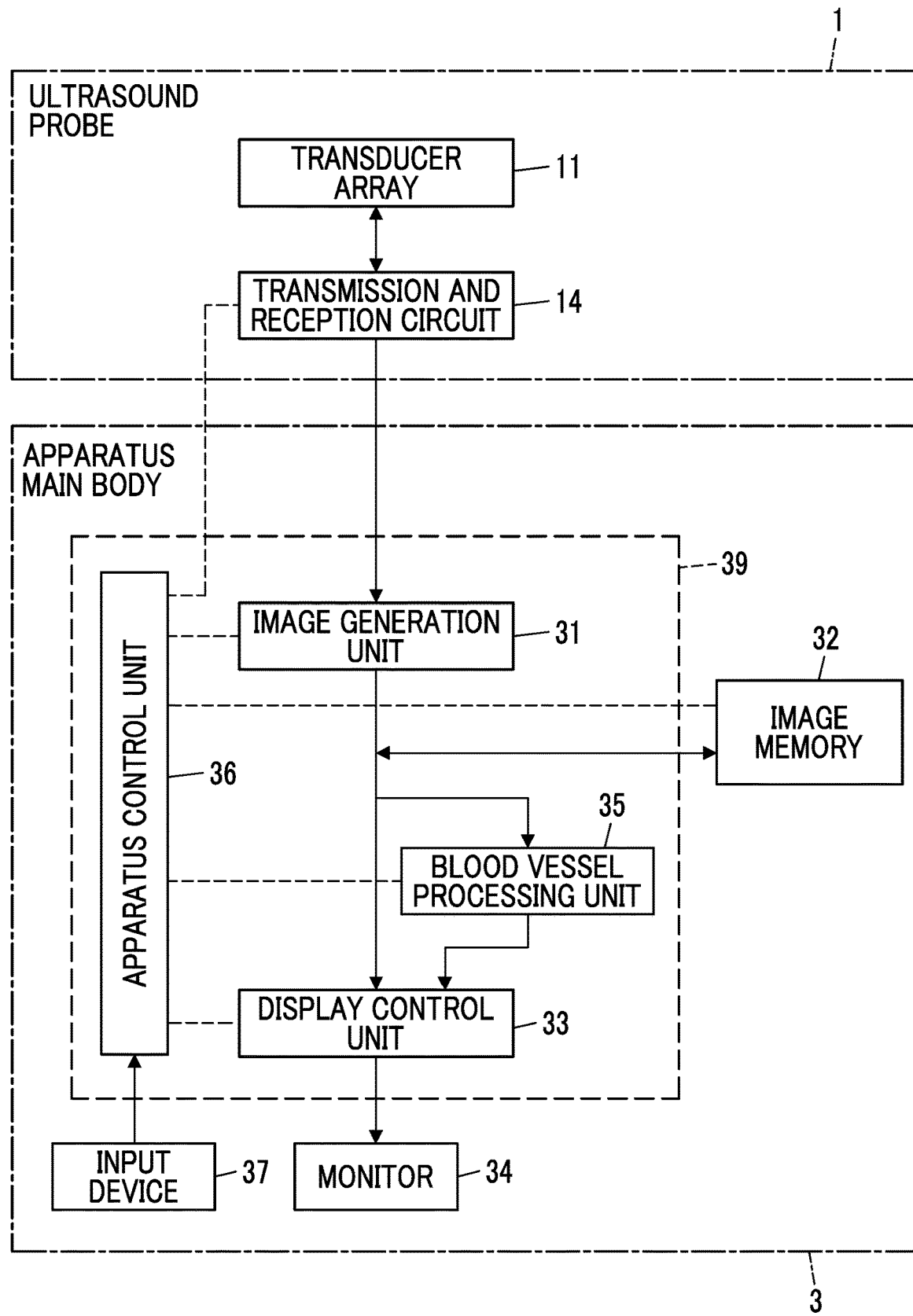
FIG. 1 is a block diagram of an embodiment illustrating a configuration of an ultrasound diagnostic apparatus.

FIG. 1 is a block diagram of an embodiment illustrating a configuration of an ultrasound diagnostic apparatus of the present invention. The ultrasound diagnostic apparatus illustrated in FIG. 1 is a stationary ultrasound diagnostic apparatus, and includes an ultrasound probe 1, and an apparatus main body 3 connected to the ultrasound probe 1.

The ultrasound probe 1 scans an examination location of a subject using an ultrasound beam, and outputs a sound ray signal corresponding to an ultrasound image of the examination location. As illustrated in FIG. 1, the ultrasound probe 1 includes a transducer array 11, and a transmission and reception circuit 14. The transducer array 11 and the transmission and reception circuit 14 are bidirectionally connected to each other. Further, an apparatus control unit 36 of the apparatus main body 3 which will be described later is connected to the transmission and reception circuit 14.

The transducer array 11 has a plurality of ultrasonic transducers arranged in a one-dimensional or two-dimensional manner. According to a drive signal supplied from the transmission and reception circuit 14, each of the transducers transmits an ultrasonic wave and receives a reflected wave from the subject to output an analog reception signal.

For example, each transducer is formed by using an element in which electrodes are formed at both ends of a piezoelectric body consisting of piezoelectric ceramic represented by lead zirconate titanate (PZT), a polymer piezoelectric element represented by poly vinylidene di fluoride (PVDF), piezoelectric single crystal represented by lead magnesium niobate-lead titanate (PMN-PT), or the like.

Figure 2:
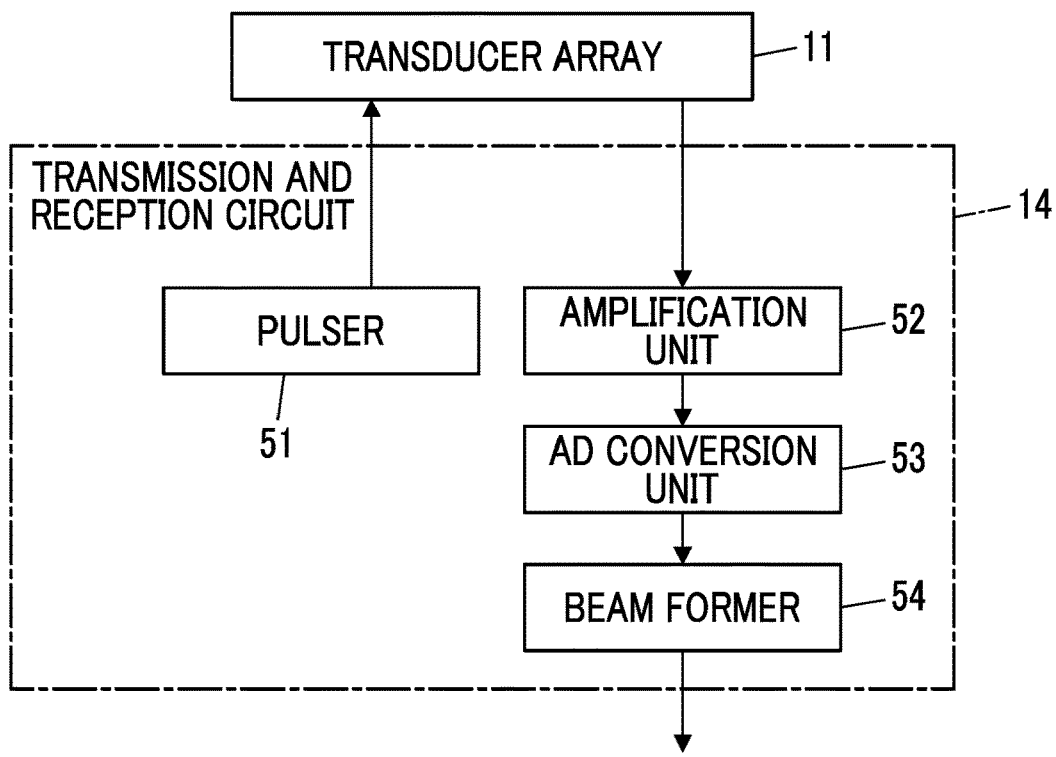
FIG. 2 is a block diagram of an embodiment illustrating a configuration of a transmission and reception circuit.

The transmission and reception circuit 14 causes the transducer array 11 to transmit the ultrasonic wave, and performs reception focusing processing on the reception signal output from the transducer array 11 that has received the ultrasound echo to generate a sound ray signal, under the control of the apparatus control unit 36. As illustrated in FIG. 2, the transmission and reception circuit 14 has a pulser 51 connected to the transducer array 11, and an amplification unit 52, an analog digital (AD) conversion unit 53, and a beam former 54 that are sequentially connected in series from the transducer array 11.

The pulser 51 includes, for example, a plurality of pulse generators, and the pulser 51 adjusts the amount of delay of each drive signal so that ultrasonic waves transmitted from the plurality of transducers of the transducer array 11 form an ultrasound beam on the basis of a transmission delay pattern selected by the apparatus control unit 36, and supplies the obtained signals to the plurality of transducers. Thus, in a case where a pulsed or continuous-wave voltage is applied to the electrodes of the transducers of the transducer array 11, the piezoelectric body expands and contracts to generate pulsed or continuous-wave ultrasonic waves from each transducer. From the combined wave of these ultrasonic waves, an ultrasound beam is formed.

The transmitted ultrasound beam is reflected by a target, for example, a site of the subject, and propagates toward the transducer array 11 of the ultrasound probe 1. Each transducer constituting the transducer array 11 expands and contracts by receiving the ultrasound echo propagating toward the transducer array 11 in this manner, to generate the reception signal that is an electric signal, and outputs the reception signal to the amplification unit 52.

The amplification unit 52 amplifies the signals input from each transducer constituting the transducer array 11, and transmits the amplified signals to the AD conversion unit 53. The AD conversion unit 53 converts the analog signal transmitted from the amplification unit 52 into digital reception data, and outputs the reception data to the beam former 54.

The beam former 54 performs so-called reception focusing processing in which addition is performed by giving delays to respective pieces of the reception data converted by the AD conversion unit 53 according to a sound speed distribution or a sound speed set on the basis of a reception delay pattern selected by the apparatus control unit 36. Through the reception focusing processing, a sound ray signal in which each piece of the reception data converted by the AD conversion unit 53 is phased and added and the focus of the ultrasound echo is narrowed is generated.

Next, the apparatus main body 3 generates an ultrasound image of the examination location of the subject on the basis of the sound ray signal generated by the ultrasound probe 1, and displays the ultrasound image of the examination location of the subject. As illustrated in FIG. 1, the apparatus main body 3 includes an image generation unit 31, an image memory 32, a blood vessel processing unit 35, a display control unit 33, a monitor (display unit) 34, an input device 37, and the apparatus control unit 36.

The image generation unit 31 is connected to the transmission and reception circuit 14, and the display control unit 33 and the monitor 34 are sequentially connected in series to the image generation unit 31. Each of the image memory 32 and the blood vessel processing unit 35 is connected to the image generation unit 31, and the display control unit 33 is connected to the image memory 32 and the blood vessel processing unit 35. The apparatus control unit 36 is connected to the transmission and reception circuit 14, the image generation unit 31, the display control unit 33, the image memory 32, and the blood vessel processing unit 35, and the input device 37 is connected to the apparatus control unit 36.

Figure 3:
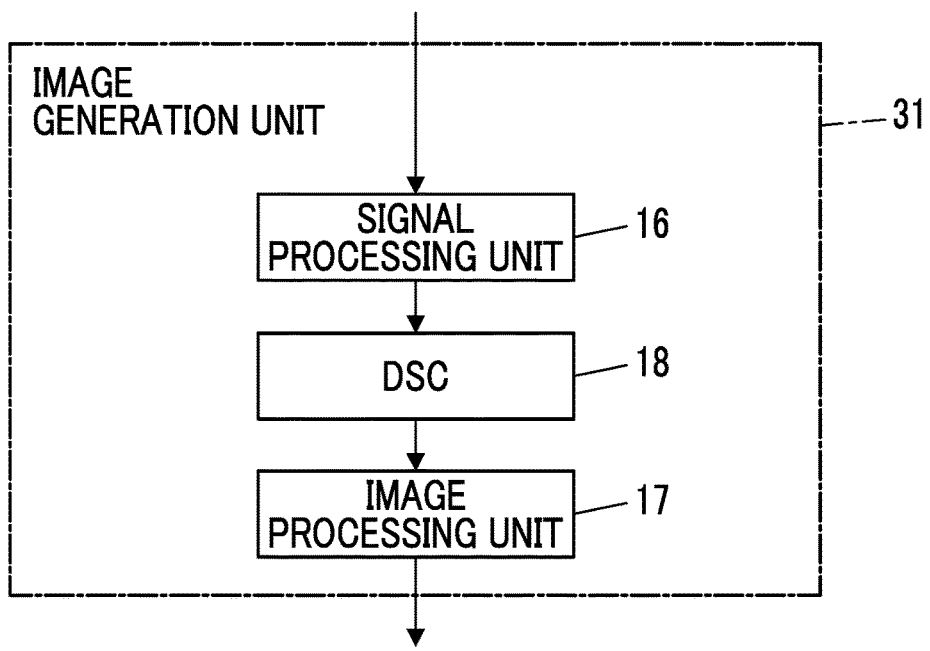
FIG. 3 is a block diagram of an embodiment illustrating a configuration of an image generation unit.

The image generation unit 31 generates the ultrasound image (ultrasound image signal) including the short-axis image of the blood vessel of the examination location of the subject, from the reception signal obtained by performing transmission and reception of the ultrasound beams with respect to the examination location of the subject using the ultrasound probe 1 (more precisely, transducer array 11), in other words, from the sound ray signal generated from the reception signal by the transmission and reception circuit 14, under the control of the apparatus control unit 36. As illustrated in FIG. 3, the image generation unit 31 has a configuration in which a signal processing unit 16, a digital scan converter (DSC) 18, and an image processing unit 17 are sequentially connected in series.

The signal processing unit 16 generates image information data corresponding to the ultrasound image on the basis of the sound ray signal generated by the transmission and reception circuit 14. More specifically, the signal processing unit 16 generates the image information data representing tomographic image information regarding tissues inside the subject, by performing envelope detection processing after signal processing, for example, correcting the attenuation of the sound ray signal generated by the beam former 54 of the transmission and reception circuit 14, which is caused by the propagation distance according to the depth of the reflection position of the ultrasonic wave.

The DSC 18 raster-converts the image information data generated by the signal processing unit 16 into an image signal according to a normal television signal scanning method.

The image processing unit 17 performs various kinds of image processing such as brightness correction, gradation correction, sharpness correction, image size correction, refresh rate correction, scanning frequency correction, and color correction according to a display format of the monitor 34, on the image signal input from the DSC 18 to generate the ultrasound image (ultrasound image signal), and then outputs the ultrasound image on which the image processing has been performed, to the image memory 32, the blood vessel processing unit 35, and the display control unit 33.

The image memory 32 is a memory that stores ultrasound images (ultrasound image signal) of the series of a plurality of frames, which are generated for each examination location by the image generation unit 31, under the control of the apparatus control unit 36. Here, as the image memory 32, recording media such as a flash memory, a hard disk drive (HDD), a solid state drive (SSD), a flexible disc (FD), a magneto-optical disc (MO disc), a magnetic tape (MT), a random access memory (RAM), a compact disc (CD), a digital versatile disc (DVD), a secure digital card (SD card), and a universal serial bus memory (USB memory), an external server, or the like can be used.

Figure 4:
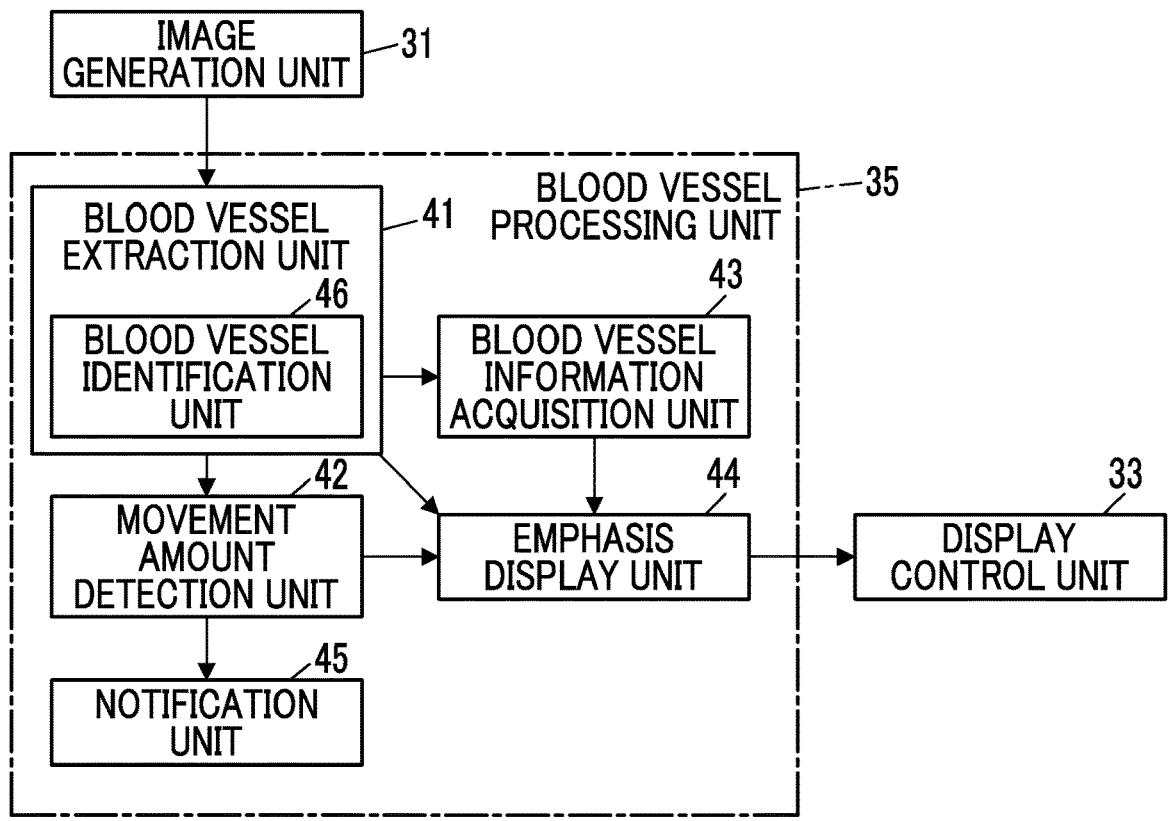
FIG. 4 is a block diagram of an embodiment illustrating a configuration of a blood vessel processing unit.

The blood vessel processing unit 35 performs various kinds of processing for displaying in an emphasized manner the blood vessel in the ultrasound image of the examination location of the subject, under the control of the apparatus control unit 36. As illustrated in FIG. 4, the blood vessel processing unit 35 has a blood vessel extraction unit 41, a movement amount detection unit 42, a blood vessel information acquisition unit 43, an emphasis display unit 44, and a notification unit 45.

The blood vessel extraction unit 41 is connected to the image generation unit 31, and each of the movement amount detection unit 42, the blood vessel information acquisition unit 43, and the emphasis display unit 44 is connected to the blood vessel extraction unit 41. The emphasis display unit 44 is connected to the blood vessel information acquisition unit 43, and the display control unit 33 is connected to the emphasis display unit 44. The notification unit 45 is connected to the movement amount detection unit 42.

The blood vessel extraction unit 41 extracts a short-axis image of the blood vessel from an ultrasound image by analyzing the ultrasound image generated by the image generation unit 31, under the control of the apparatus control unit 36.

Here, the short-axis image of the blood vessel is an image of a cross section obtained by slicing the blood vessel in a cross-sectional direction perpendicular to a traveling direction of the blood vessel. Therefore, the short-axis image of the blood vessel represents a region (blood vessel region) of the cross section in the cross-sectional direction of the blood vessel.

The blood vessel extraction unit 41 of the present embodiment has a blood vessel determination model for determining (predicting) the short-axis image of the blood vessel from the ultrasound image, and determines the short-axis image of the blood vessel included in the ultrasound image by using the blood vessel determination model.

The blood vessel determination model is a trained model that has learned, using learning ultrasound images including short-axis images of blood vessels of any subject as teacher data, a relationship between the learning ultrasound image and the short-axis image of the blood vessel included in the learning ultrasound image, for a plurality of pieces of the teacher data.

The blood vessel determination model uses an ultrasound image that is a determination target as an input, and outputs a determination result (prediction result) of the short-axis image of the blood vessel included in the ultrasound image on the basis of the training result.

The blood vessel determination model may output a determination result that the region is the short-axis image of the blood vessel, or may output a determination result of what percentage the probability that the region is the short-axis image of the blood vessel is. The blood vessel extraction unit 41 extracts the short-axis image of the blood vessel from the ultrasound image on the basis of the determination result by the blood vessel determination model.

A method of extracting the short-axis image of the blood vessel is not limited to the method of determining the short-axis image of the blood vessel using the blood vessel determination model, and for example, can use various methods of extracting the short-axis image of the blood vessel from the ultrasound image, such as a method of using template matching.

In a case where the short-axis image of the blood vessel is extracted using the template matching, the blood vessel extraction unit 41 can store typical pattern data of the short-axis image of the blood vessel in advance as a template, and calculate a similarity degree for the pattern data while searching an ultrasound image U using the template. Then, the blood vessel extraction unit 41 extracts the short-axis image of the blood vessel, assuming that there is the short-axis image of the blood vessel at a location where the similarity degree is equal to or greater than a predetermined threshold value and is maximized.

The blood vessel extraction unit 41 of the present embodiment has a blood vessel identification unit 46 that identifies blood vessels included in the ultrasound images over a plurality of frames.

The blood vessel identification unit 46 determines whether or not the blood vessel included in each of ultrasound images of adjacent frames is the same blood vessel on the basis of the short-axis image of the blood vessel extracted from each of the ultrasound images of the adjacent frames.

The blood vessel extraction unit 41 displays in an emphasized manner the short-axis image of the blood vessel determined to be the same by the blood vessel identification unit 46 over the ultrasound images of the plurality of frames.

For example, the blood vessel identification unit 46 can identify the blood vessel on the basis of at least one of a blood vessel diameter, a blood vessel label representing the type of the blood vessel (artery or vein), the relative positional relationship of a plurality of blood vessels, or the tissue information regarding the tissues around the blood vessel.

For example, a blood vessel with a blood vessel diameter of 2 mm and a blood vessel with a blood vessel diameter of 5 mm are clearly different. Therefore, the blood vessel diameter can be calculated, and the blood vessel can be identified on the basis of whether or not the blood vessel diameter of the blood vessel as the observation target has a length within a predetermined range.

Further, since the artery and the vein are never replaced with each other, the blood vessel label can be added to the blood vessel, and the blood vessel can be identified on the basis of whether or not the blood vessel label is the same.

In a case where short-axis images of a plurality of blood vessels are included in the ultrasound image, the blood vessel can be identified on the basis of the relative positional relationship of the short-axis images of the plurality of blood vessels.

The blood vessel can be identified on the basis of the tissue information regarding the tissues around the blood vessel included in the ultrasound image, for example, nerves, muscles, and bones.

It is not essential to identify the blood vessel, but in a case where the movement amount of the ultrasound image is increased, the blood vessel as the observation target may be replaced with another blood vessel in the ultrasound image of the next frame. Therefore, it is desirable to identify the blood vessel.

The blood vessel information acquisition unit 43 acquires the blood vessel information regarding the blood vessel included in the ultrasound image by analyzing the ultrasound image generated by the image generation unit 31 on the basis of the short-axis image of the blood vessel extracted by the blood vessel extraction unit 41, under the control of the apparatus control unit 36.

Here, the blood vessel information is not particularly limited, and includes, for example, information such as the diameter of the blood vessel, the depth of the blood vessel, and the type of the blood vessel.

For example, the blood vessel information acquisition unit 43 can measure the width of the short-axis image of the blood vessel in the depth direction of the ultrasound image as the diameter of the short-axis image of the blood vessel.

Further, for example, the blood vessel information acquisition unit 43 can measure the shortest distance from the epidermis of the subject, that is, the shallowest position of the ultrasound image (upper end portion of the ultrasound image) to the short-axis image of the blood vessel in the depth direction, as the depth of the short-axis image of the blood vessel.

The blood vessel information acquisition unit 43 can identify whether the blood vessel is an artery or a vein from the blood flow direction obtained using the Doppler method.

The blood vessel information acquisition unit 43 can identify whether the blood vessel is an artery or a vein on the basis of the roundness of the short-axis image of the blood vessel. Since arteries have a high internal pressure and veins have a lower internal pressure than arteries, a blood vessel of which the roundness is equal to or greater than a predetermined threshold value can be identified as an artery, and a blood vessel of which the roundness is less than a predetermined threshold value can be identified as a vein.

Furthermore, the blood vessel information acquisition unit 43 can identify, on the basis of the tissue information regarding the tissues around the blood vessel included in the ultrasound image, whether or not the blood vessel is an artery or a vein from the fact that the arteries and veins travel in a predetermined direction around the tissues.

The emphasis display unit 44 displays in an emphasized manner the short-axis image of the blood vessel extracted by the blood vessel extraction unit 41, in the ultrasound image displayed on the monitor 34 by the control of the display control unit 33, under the control of the apparatus control unit 36. In other words, the emphasis display unit 44 creates a graphic for displaying in an emphasized manner the short-axis image of the blood vessel, and superimposes and displays the graphic in the ultrasound image displayed on the monitor 34.

The method of displaying in an emphasized manner the short-axis image of the blood vessel is not particularly limited, but for example, a region including the short-axis image of the blood vessel may be surrounded by an enclosing line with an arbitrary shape such as a circular shape or square shape, or a region within the short-axis image of the blood vessel may be hatched. Further, the enclosing line and hatching may be colored in any color, or may be of any line type. Alternatively, the short-axis image of the blood vessel may be displayed in an emphasized manner by making the region within the short-axis image of the blood vessel a different color or lightness than other regions in the ultrasound image.

The emphasis display unit 44 can display the blood vessel information regarding the blood vessel acquired by the blood vessel information acquisition unit 43 as the annotation on the monitor 34 in addition to the emphasis display of the short-axis image of the blood vessel.

The display method of the blood vessel information is not particularly limited, but the blood vessel information can be superimposed and displayed in the ultrasound image as character information in association with the short-axis image of the blood vessel.

As the blood vessel information, the color and line type of the above-described enclosing line and hatching may be changed between the short-axis image of the artery and the short-axis image of the vein such that it is possible to identify whether the blood vessel is an artery or a vein. The colors for coloring the short-axis image of the artery and the short-axis image of the vein may be different from each other, such as coloring the short-axis image of the artery in red and the short-axis image of the vein in blue, or the lightness may be changed between the short-axis image of the artery and the short-axis image of the vein.

The movement amount detection unit 42 detects the movement amount of the ultrasound image between adjacent frames on the basis of the ultrasound images generated by the image generation unit 31.

The detection method of the movement amount is not particularly limited, but for example, the movement amount detection unit 42 can detect the movement amount by tracking the short-axis images of one blood vessel as the observation target over the ultrasound images of the plurality of frames.

In this case, in a case where the movement amount is less than the predetermined threshold value, for example, less than a first threshold value to be described later, the blood vessel extraction unit 41 detects the short-axis image of one blood vessel as the observation target described above from among the short-axis images of the blood vessels extracted from the ultrasound image. For example, in the ultrasound image displayed on the monitor 34, the blood vessel extraction unit 41 can detect a blood vessel, which is closest to the central portion in a direction orthogonal to the depth direction of the ultrasound image and is at the shallowest position in the depth direction of the ultrasound image, as the blood vessel (representative blood vessel) as the observation target.

Further, in a case where the short-axis images of the plurality of blood vessels are extracted from the ultrasound image, the movement amount detection unit 42 may detect the average value of the movement amounts of the short-axis images of the plurality of blood vessels as the movement amount of the ultrasound image.

The movement amount detection unit 42 may detect the difference (movement amount) between the central coordinates or the barycentric coordinates of the short-axis image of the blood vessel extracted from each of the ultrasound images of the adjacent frames, as the movement amount of the ultrasound image, or may detect the difference between coordinates of the feature point included in each of the ultrasound images of the adjacent frames, as the movement amount of the ultrasound image. Here, the feature point is a single or a plurality of points obtained by extracting any structure with features in anatomical structures in the ultrasound image and being specified from the structure.

Alternatively, the movement amount detection unit 42 may detect an optical flow of the ultrasound image between adjacent frames as the movement amount of the ultrasound image.

The notification unit 45 notifies the user of notification information regarding the movement speed of the ultrasound probe 1 on the basis of the movement amount of the ultrasound image detected by the movement amount detection unit 42, under the control of the apparatus control unit 36.

The method of notifying the user of the notification information is not particularly limited, but for example, a message of the notification information may be displayed on the monitor 34, a voice for reading the message may be output from a speaker (not illustrated), or both the methods may be performed at the same time.

The display control unit 33 displays various kinds of information on the monitor 34 under the control of the apparatus control unit 36. For example, the display control unit 33 performs predetermined processing on the ultrasound image generated by the image generation unit 31 or the ultrasound image held in the image memory 32, and displays the processed ultrasound image on the monitor 34.

The monitor 34 displays various kinds of information under the control of the display control unit 33. For example, the monitor 34 displays the ultrasound image, the blood vessel information, the information regarding the movement speed of the ultrasound probe 1, and the like. Examples of the monitor 34 include a display device such as a liquid crystal display (LCD), and an organic electroluminescence (EL) display.

The input device 37 receives various instructions input from the user (examiner) of the ultrasound diagnostic apparatus. Although not particularly limited, the input device 37 includes various buttons, and a touch panel or the like through which various instructions are input by the user performing a touch operation.

The apparatus control unit 36 controls the ultrasound probe 1 and each unit of the apparatus main body 3 on the basis of a program stored in advance and an instruction or the like of the user input from the input device 37.

The image generation unit 31, the blood vessel processing unit 35, the display control unit 33, and the apparatus control unit 36 constitute a terminal-side processor 39.

Figure 5:
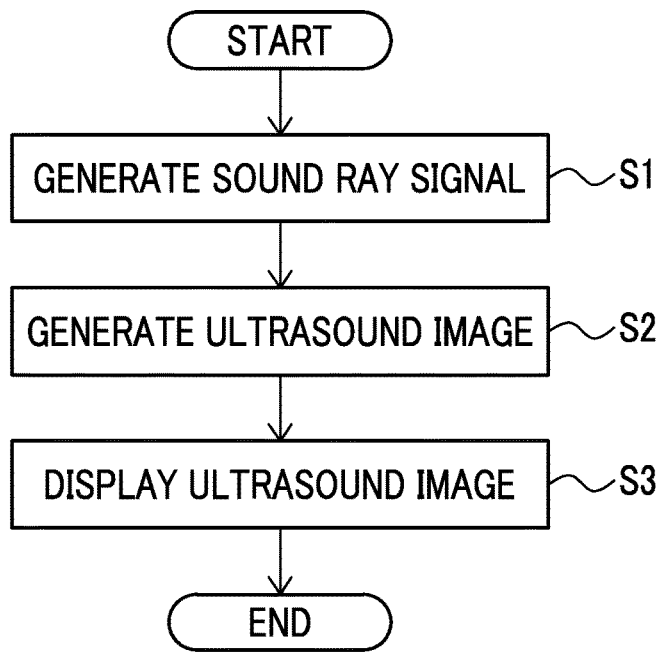
FIG. 5 is a flowchart of an embodiment illustrating an operation of an ultrasound diagnostic apparatus in a case of capturing an ultrasound image.

Next, the operation of the ultrasound diagnostic apparatus in a case where the ultrasound image is captured will be described with reference to the flowchart of FIG. 5.

First, in a state where the ultrasound probe 1 is in contact with the examination location of the subject, under the control of the apparatus control unit 36, the transmission of the ultrasonic waves is started by the transmission and reception circuit 14, and the sound ray signal is generated (Step S1).

That is, the ultrasound beams are transmitted to the examination location of the subject from a plurality of transducers of the transducer array 11 according to the drive signals from the pulser 51.

Ultrasound echoes from the examination location based on the ultrasound beams transmitted from the pulser 51 are received by each transducer of the transducer array 11, and the reception signal as an analog signal is output from each transducer of the transducer array 11, which has received the ultrasound echo.

The reception signal output from each transducer of the transducer array 11 is amplified by the amplification unit 52, and is subjected to AD conversion by the AD conversion unit 53, and thereby the reception data is acquired.

By performing the reception focusing processing on the reception data by the beam former 54, the sound ray signal is generated.

Next, under the control of the apparatus control unit 36, the ultrasound image (ultrasound image signal) of the examination location of the subject is generated by the image generation unit 31 on the basis of the sound ray signal generated by the beam former 54 of the transmission and reception circuit 14 (Step S2).

That is, the sound ray signal generated by the beam former 54 is subjected to various kinds of signal processing by the signal processing unit 16, and the image information data representing tomographic image information regarding tissues inside the subject is generated.

The image information data generated by the signal processing unit 16 is raster-converted by the DSC 18, and is further subjected to various kinds of image processing by the image processing unit 17, and thus the ultrasound image (ultrasound image signal) is generated.

The ultrasound image generated by the image processing unit 17 is held in the image memory 32.

Next, under the control of the apparatus control unit 36, predetermined processing is performed on the ultrasound image generated by the image processing unit 17 or the ultrasound image held in the image memory 32 by the display control unit 33, and the processed ultrasound image is displayed on the monitor 34 (Step S3).

Figure 6:
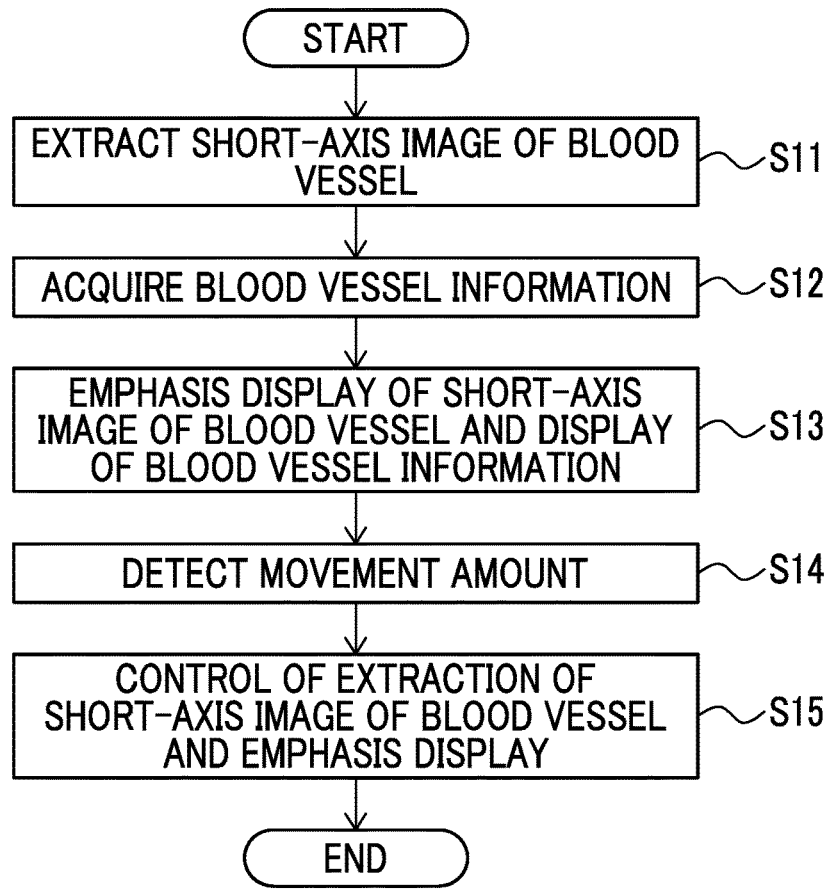
FIG. 6 is a flowchart of an embodiment illustrating an operation of an ultrasound diagnostic apparatus in a case of displaying in an emphasized manner a short-axis image of a blood vessel included in an ultrasound image.

Next, the operation of the ultrasound diagnostic apparatus in a case of displaying in an emphasized manner the short-axis image of the blood vessel included in the ultrasound image will be described with reference to the flowchart illustrated in FIG. 6.

First, by the blood vessel extraction unit 41, the ultrasound image is analyzed using the blood vessel determination model, and thereby the short-axis image of the blood vessel is extracted from the ultrasound image under the control of the apparatus control unit 36 (Step S11).

Figure 7:
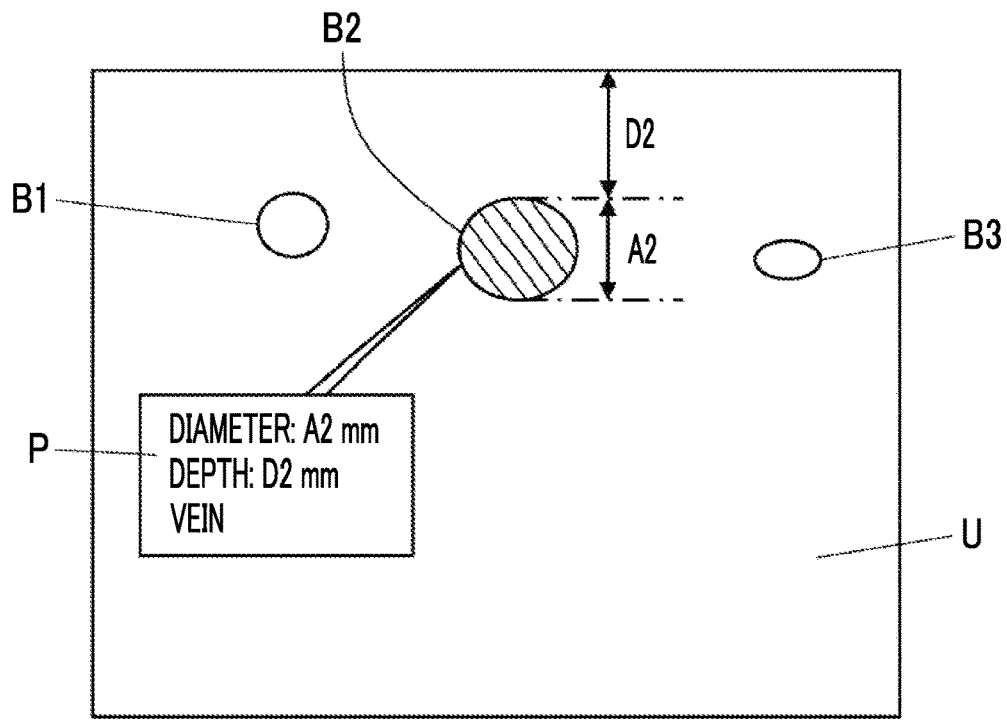
FIG. 7 is a conceptual diagram of an embodiment illustrating an ultrasound image including short-axis images of a plurality of blood vessels.

As illustrated in FIG. 7, the blood vessel extraction unit 41 extracts the short-axis image of the blood vessel included in the ultrasound image U. Here, in FIG. 7, short-axis images B1, B2, and B3 of three blood vessels are illustrated in the ultrasound image displayed on the monitor 34.

Subsequently, by the blood vessel information acquisition unit 43, the ultrasound image is analyzed, and thereby the blood vessel information regarding the blood vessel included in the ultrasound image is acquired on the basis of the short-axis image of the blood vessel extracted by the blood vessel extraction unit 41, under the control of the apparatus control unit 36 (Step S12).

For example, as illustrated in FIG. 7, the blood vessel information acquisition unit 43 measures the width of the short-axis image B2 of the blood vessel in the depth direction of the ultrasound image U, as a diameter A2 of the short-axis image B2 of the blood vessel.

The blood vessel information acquisition unit 43 measures the shortest distance from the shallowest position in the ultrasound image U to the short-axis image B2 of the blood vessel in the depth direction as a depth D2 of the short-axis image B2 of the blood vessel.

Further, the blood vessel information acquisition unit 43 identifies whether the blood vessel is an artery or a vein on the basis of at least one of the blood flow direction, the roundness of the short-axis image of the blood vessel, or the tissue information regarding the tissues around the blood vessel.

Subsequently, by the emphasis display unit 44, the short-axis image of the blood vessel extracted by the blood vessel extraction unit 41 is displayed in an emphasized manner in the ultrasound image displayed on the monitor 34, under the control of the apparatus control unit 36 (Step S13). In this case, the emphasis display unit 44 may display the blood vessel information acquired by the blood vessel information acquisition unit 43 on the monitor 34 in association with the short-axis image of the blood vessel as the observation target, in addition to the emphasis display of the short-axis image of the blood vessel.

In the present embodiment, in a case where the short-axis image of the blood vessel is displayed in an emphasized manner, first, the blood vessel identification unit 46 determines whether or not the blood vessel included in each of ultrasound images of adjacent frames is the same blood vessel on the basis of the short-axis image of the blood vessel extracted from each of the ultrasound images of the adjacent frames. Then, the blood vessel extraction unit 41 displays in an emphasized manner the short-axis image of the blood vessel determined to be the same by the blood vessel identification unit 46.

In this manner, by identifying the blood vessel, the same short-axis image of the blood vessel as the observation target can always be displayed in an emphasized manner over the ultrasound images of the plurality of frames.

As a further preferred embodiment, in a case of the emphasis display, different emphasis display methods can be used for the emphasis display method of the identified blood vessel and the emphasis display method of the unidentified blood vessel in the ultrasound image between the frames. For example, the identified blood vessel may be displayed using a solid line, and the unidentified blood vessel may be displayed using a dotted line. Alternatively, the identified blood vessel may be filled with a semi-transparent color, and the unidentified blood vessel may be simply displayed using a solid line. Further, only the identified blood vessel may be displayed in an emphasized manner.

For example, as illustrated in FIG. 7, the emphasis display unit 44 displays in an emphasized manner the short-axis image B2 of the blood vessel as the observation target, among the short-axis images B1, B2, and B3 of the blood vessels. In FIG. 7, the short-axis image B2 of the blood vessel is displayed in an emphasized manner by hatching.

As illustrated in FIG. 7, the emphasis display unit 44 superimposes and displays a blood vessel information panel P including the blood vessel information in the ultrasound image U in association with the short-axis image B2 of the blood vessel, for example. In FIG. 7, as the blood vessel information, the fact that the diameter: A2 mm, the depth: D2 mm, and the type of the blood vessel is a vein is displayed in the blood vessel information panel P.

As described above, in a case where the user inserts the puncture needle into the blood vessel, it is possible to assist the user by displaying in an emphasized manner the short-axis image of the blood vessel in the ultrasound image displayed on the monitor 34.

By the movement amount detection unit 42, the movement amount of the ultrasound image between the adjacent frames is detected on the basis of the ultrasound image under the control of the apparatus control unit 36 (Step S14).

The movement amount detection unit 42 of the present embodiment detects the difference of the central coordinates of the short-axis image of the blood vessel extracted from each of the ultrasound images of the adjacent frames, in other words, the movement amount of the short-axis image of the blood vessel as the movement amount of the ultrasound image between adjacent frames.

Subsequently, by the apparatus control unit 36, the control of the extraction of the short-axis image of the blood vessel by the blood vessel extraction unit 41, the emphasis control of the short-axis image of the blood vessel by the emphasis display unit 44, and the like is performed (Step S15).

Here, in a case where the movement amount is increased to be equal to or greater than the first threshold value after the emphasis display of the short-axis image of the blood vessel by the emphasis display unit 44 is started, the apparatus control unit 36 stops the emphasis display of the short-axis image of the blood vessel by the emphasis display unit 44. In this case, the apparatus control unit 36 may stop the display of the blood vessel information regarding the blood vessel in addition to the stop of the emphasis display of the short-axis image of the blood vessel.

As a result, even in a case where the movement amount of the ultrasound image is increased, the emphasis display will not be displayed with a large deviation from the position of the short-axis image of the blood vessel included in the ultrasound image in the real frame time, the user will not feel discomfort.

Further, in a case where the movement amount is equal to or greater than the first threshold value after the emphasis display of the short-axis image of the blood vessel by the emphasis display unit 44 is started, the apparatus control unit 36 may cause the notification unit 45 to notify the notification information, in addition to stopping the emphasis display of the short-axis image of the blood vessel.

For example, on the upper right portion of the display screen of the monitor 34, notification information such as "the movement of the probe is fast, please slow it down" and "blood vessel emphasis is turned off due to the fast movement of the probe" is superimposed and displayed in the ultrasound image.

Here, by simply stopping the emphasis display of the short-axis image of the blood vessel, the user cannot intuitively know whether the function of displaying in an emphasized manner the short-axis image of the blood vessel is in an on state or an off state, or is in an on state but the emphasis display of the short-axis image of the blood vessel is temporarily stopped. On the other hand, as described above, by linking the emphasis display of the short-axis image of the blood vessel and the notification of the notification information, the user can intuitively understand the state of the function of displaying in an emphasized manner the short-axis image of the blood vessel.

Subsequently, after the movement amount is equal to or greater than the first threshold value and thus the emphasis display of the short-axis image of the blood vessel by the emphasis display unit 44 is stopped, in a case where the movement amount is decreased to be equal to or less than a second threshold value lower than the first threshold value, the apparatus control unit 36 restarts the emphasis display of the short-axis image of the blood vessel by the emphasis display unit 44. In this case, the apparatus control unit 36 may restart the display of the blood vessel information regarding the blood vessel in addition to the restart of the emphasis display of the short-axis image of the blood vessel.

Further, the apparatus control unit 36 stops the notification of the notification information by the notification unit 45.

By setting a first threshold value for stopping the emphasis display of the short-axis image of the blood vessel and a second threshold value for restarting the emphasis display of the short-axis image of the blood vessel to different values as in a hysteresis curve, it is possible to prevent frequent switching between the start and stop of the emphasis display of the short-axis image of the blood vessel in the vicinity of the threshold value, and perform the switching smoothly. Further, even in a case where the emphasis display of the short-axis image of the blood vessel is stopped, the extraction of the short-axis image of the blood vessel is always performed, and therefore, the emphasis display of the short-axis image of the blood vessel can be smoothly restarted.

On the other hand, after the movement amount is equal to or greater than the first threshold value and thus the emphasis display of the short-axis image of the blood vessel by the emphasis display unit 44 is stopped, in a case where the movement amount is increased to be equal to or greater than a third threshold value greater than the first threshold value, the apparatus control unit 36 stops the extraction of the short-axis image of the blood vessel by the blood vessel extraction unit 41.

In this case, the apparatus control unit 36 may perform the notification of the notification information by the notification unit 45 in addition to the stop of the extraction of the short-axis image of the blood vessel. For example, the notification information such as "blood vessel extraction/emphasis is turned off due to the fast movement of the probe" is displayed on the monitor 34.

Further, after the movement amount is equal to or greater than the third threshold value and thus the extraction of the short-axis image of the blood vessel by the blood vessel extraction unit 41 is stopped, in a case where the movement amount is decreased to be less than the third threshold value, the apparatus control unit 36 restarts the extraction of the short-axis image of the blood vessel by the blood vessel extraction unit 41.

Further, the apparatus control unit 36 stops the notification of the notification information by the notification unit 45.

Furthermore, after the emphasis display of the short-axis image of the blood vessel by the emphasis display unit 44 is started, in a case where the movement amount is decreased to be equal to or less than a fourth threshold value that is lower than the first threshold value or even lower than the second threshold value, the apparatus control unit 36 executes the extraction of the short-axis image of the blood vessel by the blood vessel extraction unit 41 and the emphasis display of the short-axis image of the blood vessel by the emphasis display unit 44 for each ultrasound image of a predetermined plurality of frames.

As a result, it is possible to reduce the power consumption of the ultrasound diagnostic apparatus required for the extraction and the emphasis display of the short-axis image of the blood vessel.

In this case, the apparatus control unit 36 stops may perform the notification of the notification information by the notification unit 45. For example, the notification information such as "blood vessel extraction/emphasis is performed slowly due to the slow movement of the probe" is displayed on the monitor 34.

On the other hand, after the movement amount is equal to or less than the fourth threshold value and thus the extraction of the short-axis image of the blood vessel by the blood vessel extraction unit 41 and the emphasis display of the short-axis image of the blood vessel by the emphasis display unit 44 are executed for each ultrasound image of the predetermined plurality of frames, in a case where the movement amount is equal to or greater than the fourth threshold value, the apparatus control unit 36 restores the extraction of the short-axis image of the blood vessel by the blood vessel extraction unit 41 and the emphasis display of the short-axis image of the blood vessel by the emphasis display unit 44 to the frame rate before the movement amount is equal to or less than the fourth threshold.

Further, the apparatus control unit 36 stops the notification of the notification information by the notification unit 45.

Here, the values of the first to fourth threshold values are not particularly limited, but for example, the first threshold value can be set to a distance corresponding to the diameter of the blood vessel, in other words, a distance of one times the diameter of the blood vessel. Further, the second threshold value can be set to a distance of 0.5 to 0.8 times the diameter of the blood vessel, the third threshold value can be set to a distance of twice the diameter of the blood vessel, and the fourth threshold value can be set to a distance of 0.25 times the diameter of the blood vessel.

In the present invention, the emphasis display can be performed for other tissues such as nerves, muscles, and bones without being limited to the emphasis display of the short-axis image of the blood vessel. However, tissues such as nerves and muscles are more difficult to extract (identify) than blood vessels, and it is even more difficult to detect the movement amount on the basis of the tissues such as nerves and muscles. On the other hand, since the blood vessels have a characteristic shape of a substantially circular shape, the extraction and the detection of the movement amount from the ultrasound image are easier than tissues such as nerves and muscles.

Therefore, the apparatus control unit 36 may extract the other tissues from the ultrasound image, detect the movement amount thereof, and display in an emphasized manner the other tissues corresponding to the movement amount. However, it is preferable to control the start and stop of the extraction and emphasis display of the other tissues on the basis of the movement amount of the short-axis image of the blood vessel. In this case, as in the case of the short-axis image of the blood vessel, for example, in a case where the movement amount of the short-axis image of the blood vessel is equal to or greater than the first threshold value, the emphasis display of the other tissues is stopped, and in a case where the movement amount is equal to or less than the second threshold value, the emphasis display of the other tissues is restarted. The same applies to the emphasis display of the other tissues in a case where the movement amount of the short-axis image of the blood vessel is equal to or greater than the third threshold value and in a case where the movement amount of the short-axis image of the blood vessel is equal to or less than the fourth threshold value.

As a result, it is possible to perform the emphasis display of the other tissues in the same manner as the emphasis display of the short-axis image of the blood vessel.

The present invention is not limited to a stationary ultrasound diagnostic apparatus, and can be similarly applied to a portable ultrasound diagnostic apparatus in which an apparatus main body 3 is realized by a laptop terminal device, and a handheld ultrasound diagnostic apparatus in which an apparatus main body 3 is realized by a handheld terminal device such as a smartphone or a tablet personal computer (PC). The ultrasound probe 1 and the apparatus main body 3 may be connected in a wired or wireless manner. Further, the entire image generation unit 31 or only the signal processing unit 16 may be provided on the ultrasound probe 1 side, or provided on the apparatus main body 3 side.

In the apparatus of the present invention, the hardware configurations of the processing units executing various kinds of processing such as the transmission and reception circuit 14, the image generation unit 31, the display control unit 33, the blood vessel processing unit 35, and the apparatus control unit 36 may be dedicated hardware, or may be various processors or computers that execute programs.

The various processors include a central processing unit (CPU) as a general-purpose processor executing software (program) and functioning as various processing units, a programmable logic device (PLD) as a processor of which the circuit configuration can be changed after manufacturing such as a field programmable gate array (FPGA), and a dedicated electric circuit as a processor having a circuit configuration designed exclusively for executing specific processing such as an application specific integrated circuit (ASIC).

One processing unit may be configured by one of the various processors or may be configured by a combination of the same or different kinds of two or more processors, for example, a combination of a plurality of FPGAs or a combination of an FPGA and a CPU). Further, a plurality of processing units may be configured by one of various processors, or two or more of a plurality of processing units may be collectively configured by using one processor.

For example, there is a form where one processor is configured by a combination of one or more CPUs and software as typified by a computer, such as a server and a client, and this processor functions as a plurality of processing units. Further, there is a form where a processor realizing the functions of the entire system including a plurality of processing units by one integrated circuit (IC) chip as typified by a system on chip (SoC) or the like is used.

Furthermore, the hardware configurations of these various processors are more specifically electric circuitry where circuit elements, such as semiconductor elements, are combined.

The method of the present invention can be carried out, for example, by a program for causing a computer to execute each step of the method. Further, a computer-readable recording medium in which this program is recorded can also be provided.

The present invention has been described in detail, but the present invention is not limited to the above-described embodiments, and various improvements and changes may be made within a range not departing from the scope of the present invention.

EXPLANATION OF REFERENCES

1: ultrasound probe
3: apparatus main body
11: transducer array
14: transmission and reception circuit
16: signal processing unit
17: image processing unit
18: DSC
31: image generation unit
32: image memory
33: display control unit
34: monitor
35: blood vessel processing unit
36: apparatus control unit
37: input device
39: processor
41: blood vessel extraction unit
42: movement amount detection unit
43: blood vessel information acquisition unit
44: emphasis display unit
45: notification unit
46: blood vessel identification unit
51: pulser
52: amplification unit
53: AD conversion unit
54: beam former
A2: diameter
B1, B2, B3: short-axis image of blood vessel
D2: depth
P: blood vessel information panel
U: ultrasound image

What is claimed is:

1. An ultrasound diagnostic apparatus comprising:
    an ultrasound probe;
    a monitor;
    an image generation unit that generates an ultrasound image including a short-axis image of a blood vessel on the basis of a reception signal obtained by performing transmission and reception of ultrasound beams with respect to a subject using the ultrasound probe;
    a display control unit that displays the ultrasound image on the monitor;
    a blood vessel extraction unit that extracts the short-axis image of the blood vessel from the ultrasound image;
    an emphasis display unit that displays in an emphasis manner the short-axis image of the blood vessel in the ultrasound image displayed on the monitor;
    a movement amount detection unit that detects a movement amount of the ultrasound image between adjacent frames on the basis of the ultrasound image; and
    an apparatus control unit that, in a case where the movement amount is equal to or greater than a first threshold value after the emphasis display of the short-axis image of the blood vessel by the emphasis display unit is started, stops the emphasis display of the short-axis image of the blood vessel by the emphasis display unit.

2. The ultrasound diagnostic apparatus according to claim 1,
    wherein in a case where the movement amount is less than the first threshold value, the blood vessel extraction unit detects the short-axis image of the blood vessel as an observation target from the short-axis images of the blood vessels extracted from the ultrasound image, and
    the movement amount detection unit detects the movement amount by tracking the short-axis image of the blood vessel as the observation target over ultrasound images of a plurality of frames.

3. The ultrasound diagnostic apparatus according to claim 1,
    wherein in a case where short-axis images of a plurality of blood vessels are extracted from the ultrasound image, the movement amount detection unit detects an average value of movement amounts of the short-axis images of the plurality of blood vessels as the movement amount of the ultrasound image.

4. The ultrasound diagnostic apparatus according to claim 1,
wherein after the emphasis display of the short-axis image of the blood vessel by the emphasis display unit is stopped, in a case where the movement amount is equal to or less than a second threshold value lower than the first threshold value, the apparatus control unit restarts the emphasis display of the short-axis image of the blood vessel by the emphasis display unit.

5. The ultrasound diagnostic apparatus according to claim 1,
wherein after the emphasis display of the short-axis image of the blood vessel by the emphasis display unit is stopped, in a case where the movement amount is equal to or greater than a third threshold value greater than the first threshold value, the apparatus control unit stops the extraction of the short-axis image of the blood vessel by the blood vessel extraction unit.

6. The ultrasound diagnostic apparatus according to claim 1,
wherein after the emphasis display of the short-axis image of the blood vessel by the emphasis display unit is started, in a case where the movement amount is equal to or less than a fourth threshold value lower than the first threshold value, the apparatus control unit executes the extraction of the short-axis image of the blood vessel by the blood vessel extraction unit and the emphasis display of the short-axis image of the blood vessel by the emphasis display unit for each ultrasound image of a predetermined plurality of frames.

7. The ultrasound diagnostic apparatus according to claim 1,
wherein the blood vessel extraction unit includes a blood vessel identification unit that determines whether or not the blood vessel included in each ultrasound image of adjacent frames is the same blood vessel on the basis of the short-axis image of the blood vessel extracted from each ultrasound image of the adjacent frames, and displays in an emphasized manner the short-axis image of the blood vessel determined to be the same.

8. The ultrasound diagnostic apparatus according to claim 1,
wherein the movement amount detection unit detects a difference between central coordinates or barycentric coordinates of the short-axis image of the blood vessel extracted from each ultrasound image of adjacent frames, a difference between coordinates of a feature point included in each ultrasound image of the adjacent frames, or an optical flow of the ultrasound image between the adjacent frames, as the movement amount of the ultrasound image.

9. The ultrasound diagnostic apparatus according to claim 1, further comprising:
a blood vessel information acquisition unit that acquires blood vessel information regarding the blood vessel included in the ultrasound image,
wherein the emphasis display unit displays the blood vessel information on the monitor in addition to the emphasis display of the short-axis image of the blood vessel.

10. The ultrasound diagnostic apparatus according to claim 1, further comprising:
a notification unit that notifies a user of notification information regarding a movement speed of the ultrasound probe on the basis of the movement amount.

11. A control method of an ultrasound diagnostic apparatus, the control method comprising:
generating an ultrasound image including a short-axis image of a blood vessel on the basis of a reception signal obtained by performing transmission and reception of ultrasound beams with respect to a subject using an ultrasound probe;
displaying the ultrasound image on a monitor;
extracting the short-axis image of the blood vessel from the ultrasound image;
displaying in an emphasis manner the short-axis image of the blood vessel in the ultrasound image displayed on the monitor;
detecting a movement amount of the ultrasound image between adjacent frames on the basis of the ultrasound image; and
stopping, in a case where the movement amount is equal to or greater than a first threshold value after the emphasis display of the short-axis image of the blood vessel is started, the emphasis display of the short-axis image of the blood vessel.

12. The control method according to claim 11,
wherein in a case where the movement amount is less than the first threshold value, the short-axis image of the blood vessel as an observation target is detected from the short-axis images of the blood vessels extracted from the ultrasound image, and
the movement amount is detected by tracking the short-axis image of the blood vessel as the observation target over ultrasound images of a plurality of frames.

13. The control method according to claim 12,
wherein in a case where short-axis images of a plurality of blood vessels are extracted from the ultrasound image, an average value of the movement amounts of the short-axis images of the plurality of blood vessels is detected as the movement amount of the ultrasound image.

14. The control method according to claim 11,
wherein after the emphasis display of the short-axis image of the blood vessel is stopped, in a case where the movement amount is equal to or less than a second threshold value lower than the first threshold value, the emphasis display of the short-axis image of the blood vessel is restarted.

15. The control method according to claim 11,
wherein after the emphasis display of the short-axis image of the blood vessel is stopped, in a case where the movement amount is equal to or greater than a third threshold value greater than the first threshold value, the extraction of the short-axis image of the blood vessel is stopped.

16. The control method according to claim 11,
wherein after the emphasis display of the short-axis image of the blood vessel is started, in a case where the movement amount is equal to or less than a fourth threshold value lower than the first threshold value, the extraction of the short-axis image of the blood vessel and the emphasis display of the short-axis image of the blood vessel are executed for each ultrasound image of a predetermined plurality of frames.

17. The control method according to claim 11,
wherein whether or not the blood vessel included in each ultrasound image of adjacent frames is the same blood vessel is determined on the basis of the short-axis image of the blood vessel extracted from each ultrasound image of the adjacent frames, and the short-axis image of the blood vessel determined to be the same is displayed in an emphasized manner.

18. The control method according to claim 11,
wherein a difference between central coordinates or barycentric coordinates of the short-axis image of the blood vessel extracted from each ultrasound image of adjacent frames, a difference between coordinates of a feature point included in each ultrasound image of the adjacent frames, or an optical flow of the ultrasound image between the adjacent frames is detected as the movement amount of the ultrasound image.

19. The control method according to claim 11, further comprising:
acquiring blood vessel information regarding the blood vessel included in the ultrasound image,
wherein the blood vessel information is displayed on the monitor in addition to the emphasis display of the short-axis image of the blood vessel.

20. The control method according to claim 11, further comprising:
notifying a user of notification information regarding a movement speed of the ultrasound probe on the basis of the movement amount.

\* \* \* \* \*